(12) United States Patent
Hinzmann et al.

(10) Patent No.: US 11,774,438 B2
(45) Date of Patent: Oct. 3, 2023

(54) MEASUREMENT SET-UP FOR A RETURN CEMENT SUSPENSION, CONSTRUCTION SITE ARRANGEMENT HAVING A MEASUREMENT SET-UP AS WELL AS METHOD AND USE

(71) Applicant: Keller Holding GmbH, Offenbach (DE)

(72) Inventors: Uwe Hinzmann, Betzendorf (DE); Christian Thienert, Erkrath (DE); Christoph Klaproth, Aachen (DE); Frank Ludwig, Essen (DE); Reiner Otterbein, Hagen (DE)

(73) Assignee: KELLER HOLDING GMBH, Offenbach (DE)

( * ) Notice: Subject to any disclaimer, the term of this patent is extended or adjusted under 35 U.S.C. 154(b) by 255 days.

(21) Appl. No.: 17/096,921

(22) Filed: Nov. 12, 2020

(65) Prior Publication Data

US 2021/0148883 A1    May 20, 2021

(30) Foreign Application Priority Data

Nov. 14, 2019    (EP) .................................... 19209140

(51) Int. Cl.
*G01N 33/38* (2006.01)
*B28C 7/02* (2006.01)
(Continued)

(52) U.S. Cl.
CPC .......... *G01N 33/383* (2013.01); *B28C 7/024* (2013.01); *B28C 7/0418* (2013.01);
(Continued)

(58) Field of Classification Search
CPC ..... B28C 7/024; B28C 7/0418; B28C 7/0481; E02D 2250/003; E02D 2300/0018;
(Continued)

(56) References Cited

U.S. PATENT DOCUMENTS

| 6,227,039 B1 * | 5/2001 | Te'eni ..................... B28C 7/024 73/53.04 |
| 2008/0156232 A1 * | 7/2008 | Crudden ................ A01N 59/16 106/725 |

(Continued)

FOREIGN PATENT DOCUMENTS

| DE | 3712151 | 10/1988 |
| DE | 69009038 | 9/1994 |

(Continued)

OTHER PUBLICATIONS

EPO, European Search Report for EP Application No. 19209140.3, dated May 25, 2020.

(Continued)

*Primary Examiner* — Harshad R Patel
*Assistant Examiner* — Truong D Phan
(74) *Attorney, Agent, or Firm* — Hodgson Russ LLP (57) ABSTRACT

The disclosure provides a measurement set-up for a return cement suspension, a construction site arrangement with a measurement set-up, and a method which can be carried out inexpensively, reliably, and easily.

15 Claims, 2 Drawing Sheets

(51) Int. Cl.
*B28C 7/04* (2006.01)
*E02D 3/12* (2006.01)
*G01F 1/34* (2006.01)
*G01K 13/00* (2021.01)
*G01N 1/38* (2006.01)
*G01N 9/32* (2006.01)
*G01N 27/04* (2006.01)
*G01N 11/00* (2006.01)
*G01N 11/06* (2006.01)

(52) U.S. Cl.
CPC .............. *B28C 7/0481* (2013.01); *E02D 3/12* (2013.01); *G01F 1/34* (2013.01); *G01K 13/00* (2013.01); *G01N 1/38* (2013.01); *G01N 9/32* (2013.01); *G01N 11/00* (2013.01); *G01N 11/06* (2013.01); *G01N 27/04* (2013.01); *E02D 2250/003* (2013.01); *E02D 2300/0018* (2013.01); *G01N 2011/0046* (2013.01)

(58) Field of Classification Search
CPC .... E02D 3/12; E02D 5/46; G01F 1/34; G01K 13/00; G01N 1/38; G01N 11/00; G01N 11/06; G01N 2011/0046; G01N 27/04; G01N 33/383; G01N 9/32
See application file for complete search history.

(56) References Cited

U.S. PATENT DOCUMENTS

2015/0103614 A1* 4/2015 Brock .............. B01F 35/71731
366/3
2018/0328162 A1* 11/2018 Hjulstad ................. E21B 47/06

FOREIGN PATENT DOCUMENTS

| JP | S60141917 | | 7/1985 |
|---|---|---|---|
| JP | H05230827 | | 9/1993 |
| JP | 2005054492 | | 3/2005 |
| JP | 2005054492 A | * | 3/2005 |
| KR | 20090114162 A | * | 11/2009 |

OTHER PUBLICATIONS

Thienert et al., "Development and testing of an online measuring system to evaluate the Reusability of cement suspensions in the jet grouting process," Joint research project of the Study Society for Tunnels and Traffic Systems—STUVA—e.V, and Keller Grundbau GmbH, 2017.

* cited by examiner

MEASUREMENT SET-UP FOR A RETURN CEMENT SUSPENSION, CONSTRUCTION SITE ARRANGEMENT HAVING A MEASUREMENT SET-UP AS WELL AS METHOD AND USE

CROSS-REFERENCE TO RELATED APPLICATION

This application claims priority to European Patent Application No. 19209140.3, filed Nov. 14, 2019, the entire disclosure of which is incorporated herein by reference.

FIELD

The invention relates to a measurement set-up for a return cement suspension. The invention also relates to a construction site arrangement having a measurement set-up and a corresponding method.

BACKGROUND

The jet grouting method (JGM) is a form of building ground injection for creating cement-soil mixture bodies in the ground. In recent years, jet grouting work has been carried out in Germany with a large total annual volume. In the case of jet grouting work using the jet grouting method, the method results in a return flow which has a high cement fraction. This return flow is usually disposed of practically unused.

However, the document DE 690 09 038 T2 (EP 0 440 825 B1), which probably represents the closest prior art, describes a method for reusing the sludge for soil stabilisation, whereby the raw sludge released during processing is collected, processed, and reused as an injection material, namely as a hardening agent.

A substance having magnetic permeability is added to the hardening agent to be injected, and the soil stabilisation method is then carried out, in which the hardening agent is injected into the soil with the substance. The raw sludge discharged during the execution of the soil stabilisation method is collected, while a physical parameter is measured on the raw sludge which indicates the magnetic permeability of the hardening agent in the raw sludge in order to calculate herefrom the amount of hardening agent contained in the collected raw sludge.

It is the object of the invention to propose a measurement set-up for a return cement suspension, as well as a construction site arrangement with a measurement set-up for the return cement suspension and a method which can be carried out cost-effectively, reliably, and easily.

SUMMARY

The invention relates to a measurement set-up for a return cement suspension, in particular for measuring at least one main measured variable of the return cement suspension.

The return cement suspension has cement fractions and soil fractions. In particular, the return cement suspension is formed by a soil stabilisation method using the jet grouting method (JGM). In the jet grouting method, a water-based cement suspension having a cement fraction, in which other fractions can be present in addition to the cement fraction, is injected into the ground under high pressure with a drilling device, which is designed as an injection lance, for example, wherein a pressure of 100 bar or several 100 bar, for example 600 bar, is exceeded. By means of the jet stream, the soil material present, in particular, is cut open and mixed with the cement suspension, which, as an aggregate, then forms a concrete-like body with the natural soil. In the case of the jet grouting method, however, there is a return flow, which emerges at a borehole mouth, for example. This return flow is referred to as return cement suspension and has cement fractions from the original cement suspension and soil fractions from the cut open soil. Alternatively, the return cement suspension can be generated by a drilling method, wherein the water-based cement suspension is injected with the cement portion during a drilling method with the drilling device. This can be a low-pressure drilling method, for example. Even with the general drilling method, there is the return flow, which emerges, for example, at the borehole mouth. This return flow is referred to as return cement suspension and has cement fractions from the original cement suspension and soil fractions.

In addition to the cement fraction, the return cement suspension can also have other binder fractions.

In particular, the return suspension can be designed as an optionally diluted mineral building material suspension which has cement paste fractions of concretes, wherein the cement paste fractions form or help form the cement fraction.

The measurement set-up optionally has a first feeding device for feeding the return cement suspension. In a simple embodiment of the invention, the first feeding device can be designed as a storage device, such as a reservoir, in particular a tub, wherein the return cement suspension is arranged in the storage device. Alternatively, the first feeding device can also be designed as a feed line or—as will be explained below—as a receiving device. Optionally, the first feeding device with the return cement suspension forms part of the measurement set-up.

The measurement set-up optionally has a second feeding device for feeding an additive, wherein the additive preferably is designed to change the rheological properties of the return cement suspension by reacting with the cement fraction of the return cement suspension. The rheological properties are understood to mean, in particular, the flowability and/or viscosity and/or flow limit of the return cement suspension.

It is preferred that the additive interacts or reacts exclusively, or at least significantly, with the cement fraction, but not with the soil fraction, in particular fine-grain fractions of the soil, and/or not with the other binder fractions.

It is further preferred that the additive changes the rheological properties in a timely manner, i.e., in a time interval of less than 5 minutes, in particular less than 2.5 minutes, in particular less than 1 minute.

The change in the rheological properties should preferably be non-reversible in order to avoid falsification of the measurement results.

The measurement set-up has a measuring mixing device for mixing the return cement suspension with the additive to form a test suspension. For example, the first feeding device can have a first metering pump device to accelerate the return cement suspension, and the second feeding device can have a second metering pump device to accelerate the additive, wherein the accelerated fractions are mixed in a mixing device, in particular in a static mixing device. In the simplest embodiment, the mixing device and/or the measuring mixing device can be designed as a merging device for the flows of the return cement suspension and the additive. Alternatively or in addition, the merging device can comprise a nozzle or high-pressure nozzle for mixing.

Eccentric screw pumps are preferably used as metering pump devices in order to permit low-pulsation delivery.

The measurement set-up has a measurement path section for guiding the test suspension. The measuring path section is designed in particular as a line, preferably as a line with a constant flow cross-section. The test suspension flows through the measuring path section during operation.

The measurement set-up has a measurement device for measuring at least one main measurement variable of the test suspension, in particular in the measuring path section. The main measured variable is preferably dependent on the rheological properties of the test suspension.

In addition, an evaluation device is provided, wherein the evaluation device can be designed, for example, as a software module or as a digital data processing device, in particular a computer, a microcontroller or the like. The evaluation device is designed in particular, in terms of program technology and/or circuit technology, to estimate and/or determine at least one quality index for the return cement suspension as a function of the main measured variable. For this function, the evaluation device can, for example, fall back on a set of rules, tables, in particular for calibrating the measurement set-up, analytical functions, artificial neural networks, etc.

The quality index is preferably a measure of the cement fraction of the return cement suspension and/or the reactivity of the return cement suspension, in particular the reactive cement fraction in the test suspension and thus in the return cement suspension. It is known that cement with impaired or delayed strength development can behave less reactively even in the fresh, i.e., flowable, state, which can be exhibited by reduced development of heat of hydration or reduced stiffening. Thus, the change in the rheological properties of the return cement suspension and the quality index derived therefrom is a measure of the reactivity of the cement fraction in the return cement suspension. Furthermore, the quality index is a measure of the cement fraction in the return cement suspension. In summary, the quality index is, in particular, a measure of the reactive cement fraction in the return cement suspension.

Alternatively or in addition, the quality index is preferably a measure of the suitability of the return cement suspension to be mixed with an, in particular, fresh cement suspension for producing a ready-to-use mixed cement suspension. It is assumed here that the return cement suspension has a reduced cement fraction, in particular a reduced reactive cement fraction, due to the introduction of the soil fraction. By mixing with a cement suspension, in particular a fresh cement suspension, a mixed cement suspension can be produced, wherein the mixing ratio between the return cement suspension and the cement suspension is adjusted so that the mixed cement suspension is ready to use, in particular is ready to use for the jet grouting method and/or drilling method described above. This functional definition of the quality index encompasses the possible use of the quality index as it is described in connection with the construction site arrangement.

The invention has a number of advantages over the prior art:

For example, the return cement suspension or the cement suspension in its entirety does not need to be mixed with the additive, as is described in the prior art, but rather only a measured fraction of the return cement suspension needs to be mixed with the additive. This saves a significant amount of additives. Furthermore, the additive does not pollute the environment due to its low use.

The measurement set-up enables online measurement of the quality index so that the return cement suspension can be fed back into the jet grouting method in real time, and thus on the construction site, so that the disposal costs for the return cement suspension can be significantly reduced.

A further consideration of the invention is that, by measuring the induced change in the rheological properties, with the changes taking place as a function of the cement fraction, in particular the reactive cement fraction, the cement fraction, in particular the reactive cement fraction, in the return cement suspension can be reliably estimated and there is therefore the potential to feed the return cement suspension back into the jet grouting method and/or drilling method on the construction site, wherein the mixing ratio depending on the cement fraction, in particular the reactive cement fraction, ensures that the mixed cement suspension is ready for use for the jet grouting method or drilling method. In principle, it would be possible to specify the cement fraction, in particular the reactive cement fraction, using physical parameters as the quality index. However, it is also possible to select the quality index such that the cement fraction, in particular the reactive cement fraction, is described qualitatively.

It is particularly preferred that the measurement set-up can be operated continuously. Thus, the at least one quality index for the test suspension flowing through the measuring path section can be output in real time and thus can be output in real time for the return cement suspension.

In a preferred embodiment of the invention, the main measured variable is designed as a fluidic characteristic variable, in particular a change in a fluidic characteristic variable, in particular as a pressure change and/or as a change in the flow velocity in the measuring path section. The fluidic characteristic variable, in particular the pressure change or flow velocity, arises or changes in the measuring path section as a function of the rheological properties of the test suspension and thus of the return cement suspension, in particular as a function of the flowability and/or the viscosity and/or the flow limit of the test suspension or the return cement suspension. The change in pressure is particularly preferably designed as an increase in pressure or an increase in the flow velocity; in alternative embodiments, the additive can also be selected such that a pressure reduction or lowering of the flow velocity occurs.

It is possible that active and/or passive fluidic elements are arranged upstream of, within and/or downstream of the measuring path section, which result in the fluidic characteristic variable changing as a function of the rheological properties of the test suspension and thus of the return cement suspension, in particular depending on the flowability and/or the viscosity and/or the flow limit of the test suspension or the return cement suspension.

The passive fluidic elements can be designed, for example, as a throttle, deflector, etc.; the active fluidic elements can be implemented as a pump, in particular as a flow machine.

In a preferred structural embodiment of the invention, the measurement set-up has a feeding portion for feeding the test suspension to the measuring path section and a discharge portion for discharging the test suspension from the measuring path section. In particular, the feeding portion, the measuring path section and the discharge portion form a closed line.

In particular, the measuring path section is designed with a narrowed flow cross-section compared to the feeding portion and to the discharge portion. In particular, the flow cross-section of the measuring path section is designed to be smaller than the flow cross-section of the feeding portion at at least one point.

Furthermore, the flow cross-section of the measuring path section is smaller than the flow cross-section of the discharge portion at at least one point. The measuring path section preferably has a constant flow portion, wherein the constant flow portion is designed to be smaller than the flow portion of the feeding portion and the discharge portion.

Alternatively or additionally, the flow velocity in the measuring path section is greater than or equal to the flow velocity in the feeding portion and the flow velocity in the discharge portion.

Alternatively or in addition, an input throttle for reducing the flow cross-section is arranged between the feeding portion and the measuring path section and an output throttle for increasing the flow cross-section between the measuring path section and the discharge portion.

The flow cross-section of the feeding portion and of the discharge portion can be designed identically, but it can also be implemented differently.

All the alternatives mentioned in particular implement the idea of changing the fluidic characteristic variable, in particular the pressure change, in particular the pressure increase, and/or changing the flow velocity in the measuring path section in order to be able to determine or estimate the rheological properties of the test suspension, in particular the flowability and/or viscosity and/or the flow limit.

Alternatively, the measuring path section is designed with an enlarged or identical flow cross-section as compared to the feeding portion and to the discharge portion. In particular, the flow cross-section of the measuring path section is designed to be larger than the flow cross-section of the feeding portion at at least one point. Furthermore, the flow cross-section of the measuring path section is larger than the flow cross-section of the discharge portion at at least one point. The measuring path section preferably has a constant flow portion, wherein the constant flow portion is designed to be larger than the flow portion of the feeding portion and the discharge portion.

Alternatively or additionally, the flow velocity in the measuring path section is smaller than or equal to the flow velocity in the feeding portion and the flow velocity in the discharge portion.

Alternatively or in addition, an input throttle for increasing the flow cross-section is arranged between the feeding portion and the measuring path section and an output throttle for reducing the flow cross-section between the measuring path section and the discharge portion.

The flow cross-section of the feeding portion and of the discharge portion can be designed identically, but it can also be implemented differently.

All the alternatives mentioned in particular implement the idea of changing the fluidic characteristic variable, in particular the pressure change, in particular the pressure decrease, and/or changing the flow velocity in the measuring path section in order to be able to determine or estimate the rheological properties of the test suspension, in particular the flowability and/or viscosity and/or the flow limit.

In further alternatives of the invention, only one throttle may be used, optionally upstream or downstream of the measuring path section, wherein the one throttle changes the flow cross-section. It is also possible that a pump, in particular a fluid kinetic machine, is used as the fluidic element, wherein the fluidic measured variable and its change is recorded in the fluidically downstream measuring path section. It is even conceivable that no fluidic elements are used and the change in the fluidic characteristic variable is only due to the fluidic properties of the measuring path section and/or the measuring mixing device.

In one possible further development of the invention, the pressure measuring device has a first pressure sensor, with the first pressure sensor being arranged upstream of the measuring path section and/or in the feeding portion. Furthermore, the pressure measuring device has a second pressure sensor, with the second pressure sensor being arranged downstream of the measuring path section and/or in the discharge portion. A change in pressure in the measuring path section can be determined by means of these two pressure sensors. In an alternative embodiment, the pressure is only measured at one point; an arrangement of more than two pressure measuring points is also possible.

It can be provided that only a specified and/or conditioned return cement suspension is used in the measurement set-up. In order to check the boundary conditions and/or to improve the detection of the rheological properties, at least one, some, or all of the following auxiliary measured variables for determining the at least one quality index can optionally also be recorded. For this purpose, the measuring device has at least one, some, or all of the following sensor devices:

The measuring device optionally has a density sensor for measuring the density of the return cement suspension and/or test suspension as a first auxiliary measured variable. The density sensor is preferably designed as a Coriolis measuring system, since this measuring system has advantages especially with measuring materials that are high in solids and aggressive. The density of the return cement suspension varies due to the uptake of soil fractions and uptake of pore water/discharge of filtrate water in the building ground. Unless it can be ensured otherwise that the return cement suspension and/or test suspension have a constant and/or a known density, it can be detected by means of the density sensor and optionally taken into account in the estimation and/or determination of the at least one quality index.

The measuring device optionally has a temperature sensor for measuring the temperature of the return cement suspension and/or the test suspension as a second auxiliary measured variable. The temperature affects the rheological properties of the return cement suspension and/or the test suspension. Unless it can be ensured otherwise that the return cement suspension and/or test suspension have a constant and/or a known temperature, it can be detected by means of the temperature sensor and optionally taken into account in the estimation and/or determination of the at least one quality index.

The measuring device optionally has a conductivity sensor for measuring the electrical conductivity of the return cement suspension and/or the test suspension as a third auxiliary measured variable. The measuring device optionally has a pH sensor for measuring the pH value of the return cement suspension and/or the test suspension as a fourth auxiliary measured variable. It is known from other structural engineering applications that the two chemical parameters, electrical conductivity and pH value, are influenced by the cement fraction.

In order to ensure that the return cement suspension and the additive are fed into the measuring mixing device in a controlled manner, it is preferred that flow rate sensors are provided for measuring the volume flows of the return cement suspension and/or the additive.

It can be provided that the evaluation device is designed to estimate and/or determine the at least one quality index as a function of at least one, some, or all auxiliary measured variables.

The evaluation device optionally has an artificial neural network. In particular, an artificial neural network is to be understood as a deep artificial neural network. The artificial neural network has nodes, with the nodes describing weightings for further processing of a signal, for example. The artificial neural network is taught and/or teachable to determine the at least one quality index based on the main measured variable and optionally additionally at least one, some, or all auxiliary measured variables. For example, the artificial neural network is taught that the main measured variable, and optionally at least one, some, or all auxiliary measured variables, are provided as at least one input signal to the artificial neural network, and the artificial neural network, in particular in the layers and/or by means of the nodes assesses and/or evaluates the main measured variable, and optionally additionally at least one, some, or all auxiliary measured variables, in order to determine the at least one quality index as a function thereof. The artificial neural network is to be understood in particular as a classifier. The artificial neural network can represent a taught artificial neural network; alternatively and/or in addition, the artificial neural network can continue to learn in the course of the operation of the evaluation device. With regard to the topology, the artificial neural network is preferably designed as a multilayer perceptron.

In a preferred embodiment of the invention, the additive is designed as an accelerator and/or as a stabiliser, for example also as a mixture of accelerator and stabiliser. In particular, the additive is designed to interact exclusively, or at least significantly, with the cement fraction. The second feeding device preferably has the additive.

As a stabiliser, in particular a chemical stabiliser, the additive is in the form of or comprises a polymer, with the polymers affecting the viscosity of the return cement suspension. Alternatively or in addition, they can be referred to as viscosity modifying agents (VMA). After the stabilisers implement an interaction with the liquid phase, i.e., the water, or the solid phase, i.e., the cement and/or soil fraction, or with both phases, it is preferred that the stabiliser is designed to interact primarily with the cement and/or soil fraction.

When designed as an accelerator, the additive can be designed as a hardening accelerator or as a solidification accelerator. With hardening accelerators, the initial strength of concrete or the return cement suspension is increased. On the other hand, solidification accelerators are more preferred, which reduce the time until the return cement suspension changes from the plastic to the solid state. These include, for example, what are termed shotcrete accelerators. These solidification accelerators appear particularly suitable for the measurement set-up.

The additive is particularly preferably designed as a soluble glass, in particular an alkaline soluble glass. In particular, the additive is implemented as or comprises a soda soluble glass Soda soluble glass has the advantage that it stiffens the return cement suspension within less than 5 minutes, there is no premature separation and no lump formation, and that stability prevails with further mixing.

A construction site arrangement is also described herein. The construction site arrangement is used in particular to implement the drilling method and/or jet grouting method for soil stabilisation, as described above.

The construction site arrangement has a receiving device for receiving return cement suspension from a borehole. The return cement suspension is preferably designed and produced as described above.

The construction site arrangement has a supply mixing device, having a first inlet for a cement suspension, in particular a fresh cement suspension, and a second inlet for the return cement suspension. Furthermore, the supply mixing device has an outlet for supplying a drilling pump device for a drilling device. The supply mixing device is designed to mix the cement suspension and the return cement suspension in a mixing ratio, in particular in an adjustable mixing ratio, to form a mixed cement suspension.

The mixed cement suspension is discharged via the outlet and in particular fed to the drilling pump device for the drilling device.

Furthermore, the construction site arrangement has a measurement set-up for the return cement suspension, with the measurement set-up having a first and a second feeding device, as already described above.

Furthermore, the measurement set-up has a measuring mixing device for mixing the return cement suspension with the additive to form a test suspension, wherein the measuring mixing device, the additive, and the test suspension are designed as already described above.

In addition, the measurement set-up has a measurement path section for guiding the test suspension, designed as described above. The measurement set-up also comprises a measuring device as described above.

The measurement set-up has an evaluation device or is connected thereto for data purposes, wherein the evaluation device is designed, in particular in construction, like the evaluation device described above. The evaluation device is designed to estimate and/or determine at least one quality index for the return cement suspension as a function of the main measured variable.

Furthermore, the measurement set-up has a control device, wherein the control device can be designed as a software module, as an electronic data processing device, in particular as a computer, microcontroller, etc. The control device is designed to set the mixing ratio in the supply mixing device as a function of the at least one quality index. As already explained, the at least one quality index can be designed, for example, as a qualitative description of the quality of the return cement suspension. The quality index is designed to be able to determine the mixing ratio in the supply mixing device by means of the control device. In particular, the control device determines the mixing ratio such that the mixed cement suspension is ready for use for the jet grouting method for soil stabilisation, as described above.

In a preferred implementation of the invention, the control device is designed to provide the quality index in real time and/or the control device is designed to control the supply mixing device in real time. The real-time requirement is designed, in particular, such that all fractions can react quickly enough that the mixed cement suspension has the set mixing ratio so that the mixed cement suspension is ready for use.

In a possible further development of the invention, the receiving device has a separating device for separating at least part of the soil fractions from the return cement suspension. For example, the separating device is designed as a filter that sifts out coarse soil fractions. The measurement set-up is particularly preferably arranged fluidically downstream of the separating device. This design has the advantage that the measurement set-up is not blocked by coarse soil fractions. Furthermore, the return cement suspension can be better used for the supply mixing device.

Since only part of the return cement suspension needs to be checked in the measurement set-up, as a random sample so-to-speak, it is in principle possible for the measuring path section to open into a storage device so that the test suspension is disposed of, for example. However, the measuring path section is particularly preferably arranged as a bypass section between the receiving device, optionally with the separating device, and the supply mixing device. The receiving device thus forms the first feeding device. This further development has the advantage that the test suspension used for the measurement does not need to be disposed of, but is fed back into the method.

In a preferred development of the invention, the construction site arrangement has the drilling pump device and the drilling device. The drilling device can be designed, for example, as a pressure lance or as a drill.

Another subject matter of the invention is a method for producing a mixed cement suspension, in particular for a soil method and/or for a jet grouting method, in particular for soil stabilisation, which is particularly preferably carried out with the above-described measurement set-up or with the previously described construction site arrangement. The drilling method and/or jet grouting method has already been described above.

The method comprises the following steps:

Mixing a return cement suspension with an additive to produce a test suspension, wherein the additive is designed in particular as described above.

Measuring at least one main measured variable, wherein the main measured variable is dependent on the rheological properties of the test suspension, in particular as already described above. Determining at least one quality index as a function of the main measured variable, in particular as already described above. Mixing the return cement suspension with a cement suspension in a mixing ratio to form the mixed cement suspension, wherein the mixing ratio is set as a function of the quality index, in particular as already described above.

BRIEF DESCRIPTION OF THE DRAWINGS

Further features, advantages and effects of the invention will become apparent from the following description of preferred exemplary embodiments as well as the attached figures. In the figures.

DETAILED DESCRIPTION

Figure 1:
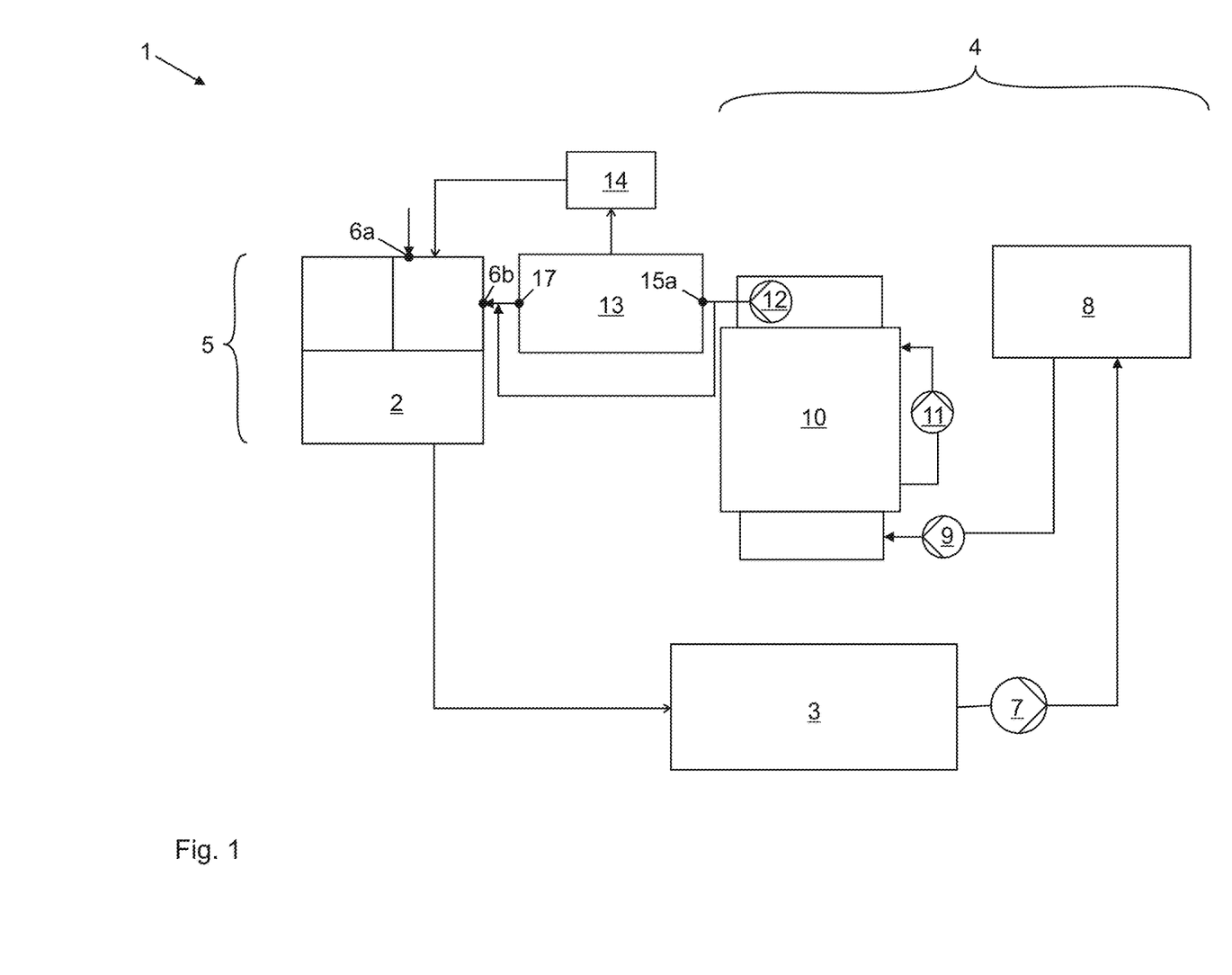
FIG. 1 shows a block diagram of a construction site arrangement as an exemplary embodiment of the invention.

FIG. 1 shows a schematic block diagram of a construction site arrangement 1 as a first exemplary embodiment of the invention. The construction site arrangement 1 needs to carry out, for example, the function of soil stabilisation, wherein soil material from the ground is cut open using a jet grouting method (JGM). Alternatively, the construction site arrangement 1 can implement any drilling method. A cement-containing suspension is used as the jet material and/or drilling material. In the exemplary embodiment, a mixed cement suspension is used as the cement-containing suspension. The cement-containing suspension is mixed with the cut open soil material, with the mixed material hardening and forming the soil stabilisation. However, with the cement-containing suspension, an additional volume is introduced into the soil, which emerges or is removed from the borehole, in particular from the borehole mouth, as return cement suspension. The return cement suspension is also created with any drilling method.

The mixed cement suspension is fed, via a drilling pump device 2, to a drilling device 3, which carries out the jet grouting method or any other drilling method. In the case of the jet grouting method, the drilling device 3 can be designed, for example, as a nozzle lance, wherein the mixed cement suspension is ejected at high pressure, in particular at a pressure greater than 100 bar, in order to cut open the soil material present.

The construction site arrangement 1 has a receiving device 4, which receives the return from a borehole of the drilling device 3 as return cement suspension. The return cement suspension thus contains cement fractions from the mixed cement suspension and soil fractions from the bottom of the borehole.

The return cement suspension is passed to a supply mixing device 5—optionally after processing. The supply mixing device 5 has a first inlet 6*a*, with the first inlet 6*a* being fluidically connected to a reservoir for a particularly mixed or fresh cement suspension so that the cement suspension can be fed into the supply mixing device 5. Furthermore, the supply mixing device has a second inlet 6*b*, with the second inlet 6*b* being fluidically connected to the receiving device 4 so that the return cement suspension can be fed into the supply mixing device 5. In the supply mixing device 5, the return cement suspension with the cement suspension is mixed at a mixing ratio to form the mixed cement suspension and is then stirred, wherein the mixed cement suspension is then fed to the drilling pump device 2.

The cement suspension is thus mixed with the recirculated return cement suspension and is fed to the drilling device 3 via the drilling pump device 2, wherein the return flow from the borehole is fed back to the supply mixing device 5 in the cycle as return cement suspension.

Due to this structure of the construction site arrangement 1, the return flow, that is to say the return cement suspension, does not produce any material that needs to be disposed of; rather the return cement suspension is kept in the cycle. However, it is possible that used material is discarded. Overall, however, a large part of the return flow and/or the return cement suspension can be recirculated and thus reused.

The receiving device 4 has a return pump device 7 which pumps the return cement suspension out of the drilling area of the drilling device 3. The return, in particular the return cement suspension, is optionally stored temporarily in a buffer tank 8. From there, the return cement suspension is pumped to a separating device 10 by a feed pump 9, wherein the separating device 10 can have a feed pump 11 for a hydrocyclone. In the separating device 10, coarse soil fractions are removed from the return cement suspension. The return cement suspension is then pumped to the second inlet 6*b* of the supply mixing device 6*b* by means of a feed pump 12. The separating device 10 can also be dispensed with in any drilling method.

It is known that the cement fraction in the return cement suspension depends on many parameters and factors. It is therefore not possible to set a static mixing ratio in the supply mixing device 5. Rather, the mixing ratio must be set as a function of the quality, in particular as a function of the cement fraction and/or the reactivity, of the return cement suspension so that the mixed cement suspension is ready for use on the construction site.

The construction site arrangement 1 has a measurement set-up 13 and a control device 14 for this purpose. At least one quality index for the quality of the return cement suspension is determined or estimated with the measurement set-up 13 and transferred to the control device 14. Knowing the quality of the cement suspension fed to the supply mixing device 5 via the first inlet 6*a* and knowing the quality of the return cement suspension from the quality index, the control device 14 can set the mixing ratio between the cement suspension and the return cement suspension so that the resulting mixed cement suspension is ready for use on the construction site. If the cement fraction and/or the reactivity of the return cement suspension is low, only a small amount of return cement suspension can be added to the cement suspension in order to obtain a ready-to-use mixed cement suspension. If, on the other hand, the cement fraction and/or the reactivity of the return cement suspension is high, more return cement suspension can be added to the cement suspension in order to obtain a ready-to-use mixed cement suspension.

The construction site arrangement 1 with the measurement set-up 13 is real-time capable so that the return cement suspension provided via the receiving device 4 can be assessed in real time and the mixing ratio can also be set in real time. This eliminates the need to initially store the return cement suspension and not just buffer it so that elaborate storage containers or even a removal of the return cement suspension from the construction site, as was previously the case, is not necessary.

The at least one quality index can be designed as a physical variable, but it can also be a qualitative variable or qualitative variables. The measurement set-up 13 is arranged fluidically downstream of the receiving device 4. At least part of the return cement suspension is passed through the measurement set-up 13, wherein the measurement set-up 13 in the exemplary embodiment in FIG. 1 is designed as a bypass to the line between the receiving device 4 and the supply mixing device 5. Because the measurement set-up 13 is arranged in a bypass to the supply line, almost no material from the return cement suspension is lost. Alternatively, it would also be possible for the fraction of the return cement suspension that flows through the measurement set-up 5 to be subsequently separated.

Figure 2:
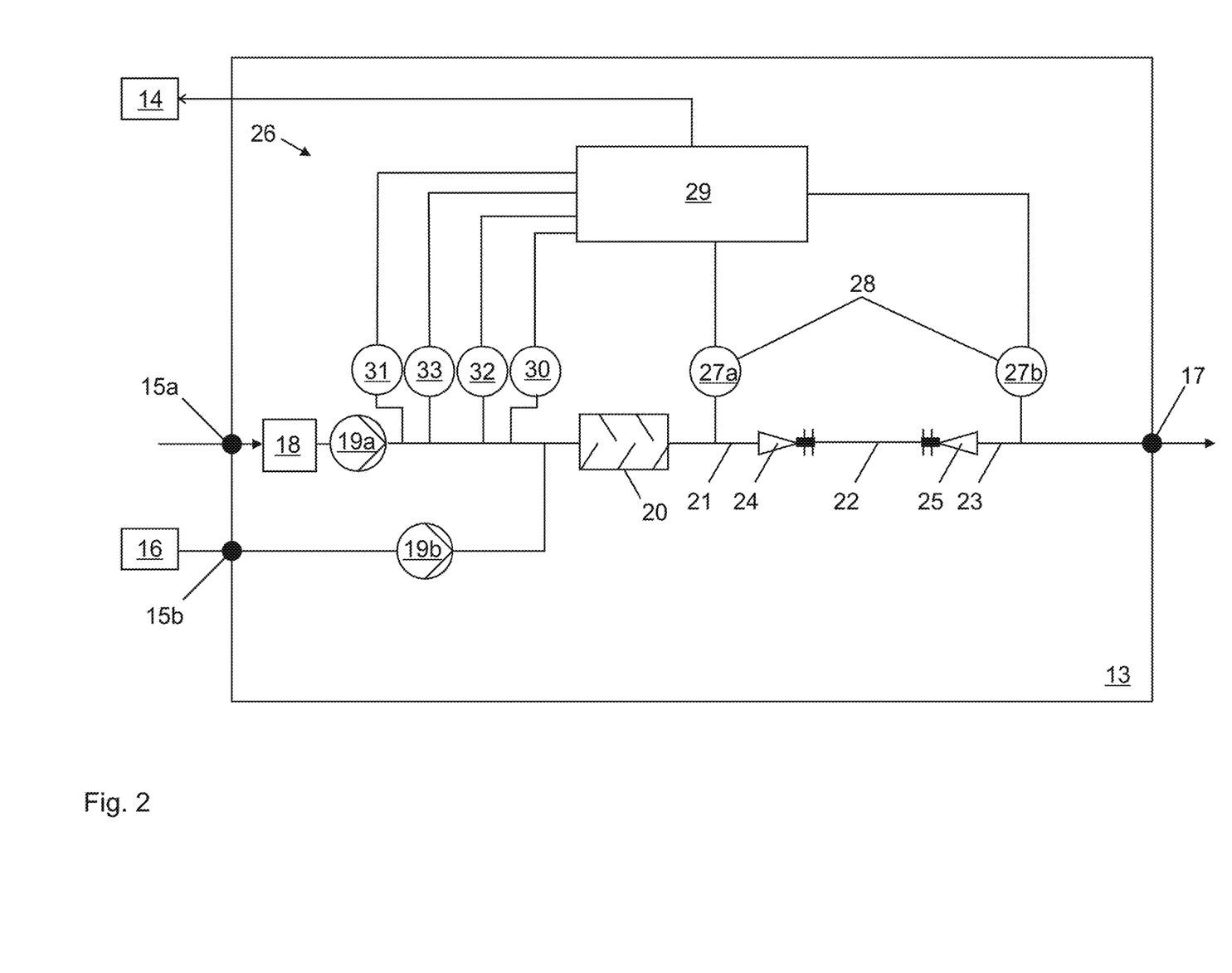
FIG. 2 shows a block diagram of a measurement set-up of the construction site arrangement as a further exemplary embodiment of the invention.

A block diagram of the measurement set-up 13 is depicted in FIG. 2. The function of the measurement set-up 13 is to record the rheological parameters of the return cement suspension or a change in rheological parameters of the return cement suspension due to a chemical modification of the return cement suspension to the test suspension and to determine the quality of the return cement suspension, in particular the cement fraction and the reactivity of the return cement suspension. The at least one quality index is then derived from the quality standard.

The measurement set-up 13 has a first feeding device 15*a* for feeding the return cement suspension, wherein the first feeding device 15*a* is designed, for example, as an inlet and is fluidically connected to the outlet of the receiving device 4. Furthermore, the measurement set-up 13 has a second feeding device 15*b*, wherein the second feeding device 15*b* is connected to or comprises a reservoir 16, with an additive being arranged in the reservoir 16. As shown in FIG. 1—an outlet 17 can be fluidically connected to the supply mixing device 5 so that the measurement set-up 13 is designed as a bypass arrangement; alternatively, the outlet 17 leads to a disposal container, not shown. Optionally, a return tank 18 with the return cement suspension is arranged in the measurement set-up 13, forming part of the first feeding device 15 *a* and designed as a buffer tank. However, since the measurement set-up 13 is intended to work in real time with respect to the return cement suspension fed parallel to the supply mixing device 5, it is preferred that the return tank 18 is designed to be very small or is completely omitted.

A first metering pump device 19*a*, which pumps the return cement suspension, is arranged downstream of the first feeding device 15*a*. A second metering pump device 19*b*, which pumps the additive, is arranged downstream of the second feeding device 15*b*. The pumps are each designed as eccentric screw pumps that work with very little pulsation.

A measuring mixing device 20 is arranged downstream, wherein the measuring mixing device 20 mixes the mixture of return cement suspension and additive, in particular homogeneously, to form a test suspension. The measuring mixing device 20 is designed in particular as a static mixing device.

The test suspension is fed, via a feeding portion 21, from the measuring mixing device 20 to a measuring path section 22 and subsequently to a discharge portion 23, with the discharge portion 23 being fluidically connected to the outlet 17. The feeding portion 21, the measuring path section 22 and the discharge portion 23 are fluidically connected to one another without outflows and inflows.

The measuring path section 22 forms a measuring section with a narrowed flow cross-section. For this purpose, an input throttle 24, which reduces the line cross-section, is arranged upstream of the measuring path section 22 and downstream of the feeding portion 21 and/or between the feeding portion 21 around the measuring path section 22. Furthermore, for this purpose, an output throttle 25, which increases the line cross-section, is arranged downstream of the measuring path section 22 and upstream of the discharge portion 23. The line cross-section in the measuring path section 22 is therefore smaller than the line cross-section in the feeding portion 21 and smaller than the line cross-section in the discharge portion 23.

From a functional point of view, the flow-related pressure changes, in particular pressure increases in a flow of the return cement suspension, are measured by means of a differential pressure measurement after adding the additive. In principle, the pressure changes as a result of stiffening, with the accompanying increase in the relevant rheological parameters, flowability/viscosity/flow limit, are the more pronounced, the greater the reactivity and/or the cement fraction. Thus, the pressure and suspension changes are measured and documented/registered within a defined measuring apparatus by means of the quantity-controlled addition of an additive.

The additive is designed in particular as a solidification accelerator, such as sodium silicate. By mixing the additive with the return cement suspension to form the test suspension, it is achieved that the rheological properties of the return cement suspension change, wherein the change in the rheological properties can be used to draw conclusions about the quality, in particular the cement fraction and/or the reactivity, in particular the reactive cement fraction of the return cement suspension. The measurement set-up 13 has a measuring device 26 with a pressure measuring device 28, with the pressure measuring device 28 recording the differential pressure between a first measuring point in the feeding portion 21 upstream of the measuring path section 22 and a second measuring point in the discharge portion 23 downstream of the measuring path section 22 as a main measured variable. The pressure measuring device 28 has a first pressure sensor 27a, with the first pressure sensor 27a being arranged fluidically upstream of the measuring path section 22 and in particular immediately upstream of the measuring path section 22, but upstream of the input throttle 24. The pressure measuring device 28 has a second pressure sensor 27b, with the second pressure sensor 27b being arranged fluidically downstream of the measuring path section 22 and in particular immediately downstream of the measuring path section 22, but downstream of the output throttle 25.

The measurement set-up 13 has an evaluation device 29, with the evaluation device 29 being designed to estimate and/or determine a quality index for the test suspension and thus for the return cement suspension, based on the pressure difference between the first and second measuring point and/or based on the pressure loss in the measuring path section 22 as the main measured variable. The quality index is a quality measure for the reactivity and/or the cement fraction in the test suspension or in the return cement suspension.

The evaluation device 29 is connected to the control device 14 for data purposes or is designed as a common device in terms of programming and/or circuit technology and supplies the quality index to the control device 14 in any form. The control device 14 sets the mixing ratio in the supply mixing device 5 as a function of the quality index. The relationship between pressure change or pressure magnitude, reactivity, cement fraction, and mixing ratio can be recorded experimentally, using characteristic curves, and adjusted. For example, look-up tables or other sets of rules can be stored in the control device 14.

Alternatively, an artificial neural network can be used in the control device 14, with the pressure difference forming an input variable for the artificial neural network.

In addition to the rheological properties, the quality of the return cement suspension depends on other parameters. Various sensors can thus be used to record auxiliary measured variables. The sensors must be used depending on the application and are only necessary if the respective parameter changes. For example, it can be useful to use a density sensor 30, a temperature sensor 31, a conductivity sensor 32, and/or a pH sensor 33. These sensors can either be integrated into the line downstream of the metering pump device 19a, or an optional manual measurement is carried out in the return tank 18. It is also possible to verify the flow rate with appropriate flow rate sensors.

The auxiliary measured variables detected from the sensors 30, 31, 32, 33 mentioned can also be fed into the evaluation device 29, in particular the artificial neural network, in order to be able to better determine the quality index.

LIST OF REFERENCE SIGNS

1 Construction site arrangement
2 Drilling pump device for the drilling rig 3
3 Drilling rig
4 Receiving device
5 Supply mixing device
6a First inlet of the supply mixing device
6b Second inlet of the supply mixing device
7 Return pump device
8 Buffer tank
9 Feed pump for
10 Separating device
11 Feed pump for hydrocyclone
12 Feed pump for supply mixing device
13 Measurement set-up
14 Control device
15a First feeding device of the measurement set-up
15b Second feeding device of the measurement set-up
16 Reservoir
17 Outlet
18 Return tank
19a First metering pump device
19b Second metering pump device
20 Measuring mixing device
21 Feeding portion
22 Measuring path section
23 Discharge portion
24 Input throttle
25 Output choke
26 Measuring device
27a First pressure sensor
27b Second pressure sensor
28 Pressure gauge device
29 Evaluation device
30 Density sensor
31 Temperature sensor
32 Conductivity sensor
33 pH sensor

What is claimed is:

1. A measurement set-up for a return cement suspension, the return cement suspension having cement fractions and soil fractions, the measurement set-up comprising:
    a measuring mixing device configured to mix a measured fraction of the return cement suspension with an additive to form a test suspension, wherein the additive is configured to change rheological properties of the return cement suspension by reacting with the cement fractions of the return cement suspension;
    a measuring path section configured to guide the test suspension;
    a measuring device configured to measure at least one main measured variable on the measuring path section, wherein the at least one main measured variable is dependent on the rheological properties of the test suspension; and
    an evaluation device, wherein the evaluation device is configured to estimate and/or determine at least one quality index for the return cement suspension as a function of the at least one main measured variable, wherein the at least one quality index describes reactivity and/or cement fraction of the return cement suspension and/or suitability for mixing of the return cement suspension with a cement suspension for generating a ready-to-use mixed cement suspension.

2. The measurement set-up according to claim 1, further comprising one or more of the following:
    a first feeding device configured to supply the return cement suspension; and
    a second feeding device configured to supply the additive.

3. The measurement set-up according to claim 2, wherein the second feeding device has the additive, wherein the additive is configured as an accelerator and/or as a stabiliser.

4. The measurement set-up according to claim 1, wherein the at least one main measured variable is a fluidic characteristic variable, including one or more of the following: a pressure change and change in flow velocity in the measuring path section.

5. The measurement set-up according to claim 1, further comprising a feeding portion configured to feed the test suspension to the measuring path section, and a discharge portion configured to discharge the test suspension from the measuring path section;

wherein one or more of the following:
a flow cross-section of the measuring path section is smaller, at least at one point, than a flow cross-section of the feeding portion, and wherein the flow cross-section of the measuring path section is smaller, at least at one point, than the flow cross-section of the discharge portion;
a flow velocity in the measuring path section is greater than a flow velocity in the feeding portion and wherein the flow velocity in the measuring path section is greater than the flow velocity in the discharge portion; and
an input throttle, configured to reduce the flow cross-section, is arranged between the feeding portion and the measuring path section and an output throttle, configured to increase the flow cross-section, is arranged between the measuring path section and the discharge portion; and wherein the measuring device has a pressure measuring device configured to determine a pressure difference in the test suspension upstream and downstream of the measuring path section and/or between the feeding portion and the discharge portion and/or a flow velocity measuring device for determining the flow velocity in the measuring path section as the at least one main measured variable.

6. The measurement set-up according to claim 5, wherein the pressure measuring device has a first pressure sensor, the first pressure sensor being arranged upstream of the measuring path section and/or in the feeding portion, and a second pressure sensor, wherein the second pressure sensor is arranged downstream of the measuring path section and/or in the discharge portion.

7. The measurement set-up according to claim 1, wherein the measuring device has a density sensor configured to measure the density of the return cement suspension and/or the test suspension as a first auxiliary measured variable and/or that the measuring device has a temperature sensor configured to measure the temperature of the return cement suspension and/or the test suspension as a second auxiliary measured variable and/or that the measuring device has a conductivity sensor configured to measure electrical conductivity of the return cement suspension and/or the test suspension as a third auxiliary measured variable and/or that the measuring device has a pH sensor configured to measure a pH value of the return cement suspension and/or the test suspension as a fourth auxiliary measured variable; and
wherein the evaluation device is configured to estimate and/or determine the at least one quality index as a function of at least one of the first auxiliary measured variable, the second auxiliary measured variable, the third auxiliary measured variable, and the fourth auxiliary measured variable.

8. The measurement set-up according to claim 1, wherein the evaluation device has an artificial neural network, wherein the artificial neural network receives at least the at least one main measured variable and optionally additionally at least one, some, or all auxiliary measured variables as input parameters and outputs the at least one quality index of the return cement suspension.

9. The measurement set-up according to claim 1, wherein the additive is or has a soluble glass.

10. A construction site arrangement comprising:
a receiving device configured to receive return cement suspension from a borehole, wherein the return cement suspension has cement fractions and soil fractions;
a supply mixing device, wherein the supply mixing device has a first inlet for a cement suspension, a second inlet for the return cement suspension, and an outlet for supplying a drilling pump device for a drilling device, wherein the supply mixing device is configured to mix the cement suspension and return cement suspension in a mixing ratio to form a mixed cement suspension;
a measurement set-up according to claim 1; and
a control device, wherein the control device is configured to set the mixing ratio in the supply mixing device as a function of the at least one quality index.

11. The construction site arrangement according to claim 10, wherein the evaluation device is configured to provide the quality index in real time and/or the control device is configured to control the supply mixing device in real time.

12. The construction site arrangement according to claim 10, wherein the receiving device has a separating device configured to separate at least part of the soil fractions from the return cement suspension.

13. The construction site arrangement according to claim 10, wherein the measuring path section is configured as a bypass portion between the receiving device and the supply mixing device and/or that the receiving device forms or comprises the first feeding device.

14. The construction site arrangement according to claim 10, further comprising the drilling pump device and/or the drilling device.

15. A method for producing a mixed cement suspension, comprising:
mixing a measured fraction of a return cement suspension, wherein the return cement suspension has cement fractions and soil fractions, with an additive for producing a test suspension, wherein the additive is configured to change rheological properties of the return cement suspension by reacting with the cement fractions of the return cement suspension;
measuring at least one main measured variable of the test suspension, wherein the at least one main measured variable is dependent on the rheological properties of the test suspension;
determining at least one quality index as a function of the at least one main measured variable, wherein the at least one quality index describes reactivity and/or cement fraction of the return cement suspension and/or suitability for mixing of the return cement suspension with a cement suspension for generating a ready-to-use mixed cement suspension; and
mixing the return cement suspension with a cement suspension in a mixing ratio to form the mixed cement suspension, wherein the mixing ratio is set as a function of the quality index.

\* \* \* \* \*